(12) United States Patent
Kuyava

(10) Patent No.: US 8,123,674 B2
(45) Date of Patent: Feb. 28, 2012

(54) CORRUGATED EXPANSION-CONSTRAINING SLEEVE FOR AN INFLATABLE PENILE PROSTHESIS CYLINDER

(75) Inventor: Charles C. Kuyava, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 565 days.

(21) Appl. No.: 12/269,183

(22) Filed: Nov. 12, 2008

(65) Prior Publication Data

US 2009/0124851 A1 May 14, 2009

Related U.S. Application Data

(60) Provisional application No. 60/987,136, filed on Nov. 12, 2007.

(51) Int. Cl.
*A61F 5/00* (2006.01)
(52) U.S. Cl. ........................................................ 600/40
(58) Field of Classification Search .............. 600/38–41
See application file for complete search history.

(56) References Cited

U.S. PATENT DOCUMENTS 3,832,996 A   9/1974 Kainberz
(Continued)

FOREIGN PATENT DOCUMENTS

DE   2537506 A1   8/1975
(Continued)

OTHER PUBLICATIONS

Abouassaly, R. et al, "Antibiotic-coated medical devices: with an emphasis on inflatable penile prosthesis", Asian J Androl. Sep. 2004; 6: 249-57.

(Continued)

*Primary Examiner* — John Lacyk
(74) *Attorney, Agent, or Firm* — Westman, Champlin & Kelly, P.A.

(57) ABSTRACT

An inflatable penile prosthesis cylinder of the present invention includes an inflatable chamber and a constraining sleeve of fabric. The inflatable chamber is configured to expand in response to an increase in pressure within the chamber. The sleeve of fabric constrains the expansion of the chamber, however, the sleeve of fabric includes a corrugation that facilitates some expansion of the sleeve.

18 Claims, 5 Drawing Sheets

U.S. PATENT DOCUMENTS

| | | |
|---|---|---|
| 3,853,122 A | 12/1974 | Strauch et al. |
| 3,893,456 A | 7/1975 | Small et al. |
| 3,954,102 A | 5/1976 | Buuck |
| 3,987,789 A | 10/1976 | Timm et al. |
| 3,991,752 A | 11/1976 | Gerow |
| 4,009,711 A | 3/1977 | Uson |
| 4,066,073 A | 1/1978 | Finney et al. |
| 4,151,840 A | 5/1979 | Barrington |
| 4,151,841 A | 5/1979 | Barrington |
| 4,177,805 A | 12/1979 | Tudoriu |
| 4,187,839 A | 2/1980 | Nuwayser et al. |
| 4,201,202 A | 5/1980 | Finney et al. |
| 4,204,530 A | 5/1980 | Finney |
| 4,222,377 A | 9/1980 | Burton et al. |
| 4,224,934 A | 9/1980 | Scott et al. |
| 4,235,227 A | 11/1980 | Yamanaka |
| 4,244,370 A | 1/1981 | Furlow et al. |
| 4,267,829 A | 5/1981 | Burton et al. |
| 4,318,396 A | 3/1982 | Finney |
| 4,342,308 A | 8/1982 | Trick |
| 4,345,339 A | 8/1982 | Muller et al. |
| 4,353,360 A | 10/1982 | Finney et al. |
| 4,360,010 A | 11/1982 | Finney |
| 4,364,379 A | 12/1982 | Finney |
| 4,369,771 A | 1/1983 | Trick |
| 4,378,792 A | 4/1983 | Finney |
| 4,383,525 A | 5/1983 | Scott et al. |
| 4,392,562 A | 7/1983 | Burton et al. |
| 4,399,811 A | 8/1983 | Finney et al. |
| 4,399,812 A | 8/1983 | Whitehead |
| 4,404,968 A | 9/1983 | Evans, Sr. |
| 4,407,278 A | 10/1983 | Burton et al. |
| 4,411,260 A | 10/1983 | Koss |
| 4,411,261 A | 10/1983 | Finney |
| 4,412,530 A | 11/1983 | Burton |
| 4,424,807 A | 1/1984 | Evans, Sr. |
| 4,441,491 A | 4/1984 | Evans, Sr. |
| 4,449,520 A | 5/1984 | Palomar |
| 4,457,335 A | 7/1984 | Trick |
| 4,483,331 A | 11/1984 | Trick |
| 4,517,967 A | 5/1985 | Timm et al. |
| 4,522,198 A | 6/1985 | Timm et al. |
| 4,523,584 A | 6/1985 | Yachia et al. |
| 4,532,920 A | 8/1985 | Finney |
| 4,541,420 A | 9/1985 | Timm et al. |
| 4,545,081 A | 10/1985 | Nestor et al. |
| 4,550,719 A | 11/1985 | Finney et al. |
| 4,550,720 A | 11/1985 | Trick |
| 4,558,693 A | 12/1985 | Lash et al. |
| 4,559,931 A | 12/1985 | Fischell |
| 4,566,446 A | 1/1986 | Fogarty |
| 4,572,168 A | 2/1986 | Fischell |
| 4,574,792 A | 3/1986 | Trick |
| 4,590,927 A | 5/1986 | Porter et al. |
| 4,594,998 A | 6/1986 | Porter et al. |
| 4,596,242 A | 6/1986 | Fischell |
| 4,602,625 A | 7/1986 | Yachia et al. |
| 4,604,994 A | 8/1986 | Sealfon |
| 4,611,584 A | 9/1986 | Finney |
| 4,619,251 A | 10/1986 | Helms et al. |
| 4,622,958 A | 11/1986 | Finney |
| 4,651,721 A | 3/1987 | Mikulich et al. |
| 4,653,485 A | 3/1987 | Fishell |
| 4,664,100 A | 5/1987 | Rudloff |
| 4,665,902 A | 5/1987 | Goff et al. |
| 4,665,903 A | 5/1987 | Whitehead |
| 4,666,428 A | 5/1987 | Mattioli et al. |
| 4,669,456 A | 6/1987 | Masters |
| 4,671,261 A | 6/1987 | Fischell |
| 4,682,583 A | 7/1987 | Burton et al. |
| 4,682,589 A | 7/1987 | Finney |
| 4,693,719 A | 9/1987 | Franko et al. |
| 4,699,128 A | 10/1987 | Hemmeter |
| 4,718,410 A | 1/1988 | Hakky |
| 4,724,830 A | 2/1988 | Fischell |
| 4,726,360 A | 2/1988 | Trick et al. |
| 4,730,607 A | 3/1988 | Fischell |
| 4,766,889 A | 8/1988 | Trick et al. |
| 4,773,403 A | 9/1988 | Daly |
| 4,782,826 A | 11/1988 | Fogarty |
| 4,790,298 A | 12/1988 | Trick |
| 4,791,917 A | 12/1988 | Finney |
| 4,807,608 A | 2/1989 | Levius |
| 4,829,990 A | 5/1989 | Thuroff et al. |
| 4,881,530 A | 11/1989 | Frick |
| 4,881,531 A | 11/1989 | Timm et al. |
| 4,895,139 A | 1/1990 | Hauschild et al. |
| 4,899,737 A | 2/1990 | Lazarian |
| 4,917,110 A | 4/1990 | Trick |
| 4,988,357 A | 1/1991 | Koss |
| 5,010,882 A | 4/1991 | Polyak et al. |
| 5,048,510 A | 9/1991 | Hauschild et al. |
| 5,050,592 A | 9/1991 | Olmedo |
| 5,062,416 A | 11/1991 | Stucks |
| 5,062,417 A | 11/1991 | Cowen |
| 5,063,914 A | 11/1991 | Cowen |
| 5,067,485 A | 11/1991 | Cowen |
| 5,101,813 A | 4/1992 | Trick |
| 5,112,295 A | 5/1992 | Zinner et al. |
| 5,114,398 A | 5/1992 | Trick et al. |
| 5,129,880 A | 7/1992 | Grundei |
| 5,141,509 A | 8/1992 | Burton et al. |
| 5,167,611 A | 12/1992 | Cowan |
| 5,171,272 A | 12/1992 | Levius |
| 5,176,708 A | 1/1993 | Frey et al. |
| 5,250,020 A | 10/1993 | Bley |
| 5,263,981 A | 11/1993 | Polyak et al. |
| 5,283,390 A | 2/1994 | Hubis et al. |
| 5,344,388 A | 9/1994 | Maxwell et al. |
| 5,433,694 A | 7/1995 | Lim |
| 5,445,594 A | 8/1995 | Elist |
| 5,509,891 A | 4/1996 | DeRidder |
| 5,512,033 A | 4/1996 | Westrum, Jr. et al. |
| 5,553,379 A | 9/1996 | Westrum, Jr. et al. |
| 5,669,870 A | 9/1997 | Elist |
| 5,704,895 A | 1/1998 | Scott et al. |
| 5,851,176 A | 12/1998 | Willard |
| 5,895,424 A | 4/1999 | Steele, Sr. et al. |
| 5,899,849 A | 5/1999 | Elist |
| 6,171,233 B1 | 1/2001 | Willard |
| 6,346,492 B1 | 2/2002 | Koyfman |
| 6,443,887 B1 | 9/2002 | Derus et al. |
| 6,533,719 B2 | 3/2003 | Kuyava et al. |
| 6,558,315 B1 | 5/2003 | Kuyava |
| 6,579,230 B2 | 6/2003 | Yachia et al. |
| 6,600,108 B1 | 7/2003 | Mydur et al. |
| 6,723,042 B2 | 4/2004 | Almli et al. |
| 6,730,017 B2 | 5/2004 | Henkel et al. |
| 6,733,527 B2 | 5/2004 | Koyfman |
| 6,929,599 B2 | 8/2005 | Westrum |
| 6,935,847 B2 | 8/2005 | Kuyava et al. |
| 6,991,601 B2 | 1/2006 | Kuyava et al. |
| 7,066,877 B2 | 6/2006 | Kuyava |
| 7,066,878 B2 | 6/2006 | Eid |
| 7,169,103 B2 | 1/2007 | Ling et al. |
| 7,244,227 B2 | 7/2007 | Morningstar |
| 7,250,026 B2 | 7/2007 | Kuyava |
| 7,350,538 B2 | 4/2008 | Kuyava et al. |
| 7,390,296 B2 | 6/2008 | Mische |
| 7,438,682 B2 | 10/2008 | Henkel et al. |
| 7,491,164 B2 | 2/2009 | Choi et al. |
| 7,637,861 B2 | 12/2009 | Kuyava et al. |
| 2002/0033564 A1 | 3/2002 | Koyfman |
| 2002/0082473 A1 | 6/2002 | Henkel et al. |
| 2002/0082709 A1 | 6/2002 | Almli et al. |
| 2002/0091302 A1 | 7/2002 | Kuyava et al. |
| 2003/0028076 A1 | 2/2003 | Kuyava et al. |
| 2004/0220447 A1 | 11/2004 | Morningstar |
| 2005/0014993 A1 | 1/2005 | Mische |
| 2006/0235267 A1 | 10/2006 | George et al. |
| 2008/0103353 A1 | 5/2008 | Jahns et al. |
| 2008/0114202 A1 | 5/2008 | Kuyava et al. |
| 2009/0105530 A1 | 4/2009 | Kuyava |
| 2009/0105818 A1 | 4/2009 | George et al. |
| 2009/0287042 A1 | 11/2009 | Almli et al. |

FOREIGN PATENT DOCUMENTS

| | | |
|---|---|---|
| EP | 0051420 | 5/1982 |
| EP | 0065853 | 12/1982 |
| EP | 0137752 B1 | 8/1989 |
| EP | 0774935 B1 | 7/1995 |
| EP | 0682923 | 11/1995 |
| EP | 0925764 | 6/1999 |
| GB | 2151484 A | 7/1985 |
| GB | 2160777 | 1/1986 |
| GB | 2192546 | 1/1988 |
| WO | WO8000302 | 3/1980 |
| WO | WO8500513 | 2/1985 |
| WO | 8601398 A1 | 3/1986 |
| WO | WO9203107 | 3/1992 |
| WO | WO9404095 | 3/1994 |
| WO | 9604865 A1 | 2/1996 |
| WO | WO02051339 | 7/2002 |

OTHER PUBLICATIONS

Agrawal, V. et al. "An audit of implanted penile prostheses in the UK",BJU International 98, 293-295 (2006).

Akin-Olugbade, O. et al, "Determinants of Patient Satisfaction Following Penile Prosthesis Surgery", J Sex Med 2006; 3: 743-48.

Al-Najar, A., et al, "Should being aged over 70 years hinder penile prosthesis implantation?", BJU International 2009 1-4.

AMS 700 CX Penile Prosthesis (Brochure) 2 pages 1999.

AMS 700 Inflatable Penile Prosthesis Product Line 45 pages (1992).

AMS (Brochure) 700 Series Tactiel (Pump 2 pages) 2004.

AMS (Brochure) Ultrex/Ultrex Plus (10 pages)(1998).

AMS Ambicor Penile Prosthesis (Brochure) 1996.

Merino, G. Atienza, "Penile Prosthesis for the treatment of erectile dysfunction" Actas Urol Esp. 2006; 30(2): 159-69.

Candela, J. et al "Three-piece inflatable penile prosthesis implantatoin: . . . " J La State Med Soc 148:296-301 (1996).

Daitch, J. et al, "Long-Term Mechanical Reliability of AMS 700 Series Inflatable Penile Prostheses: Comparison . . . " J. Urol. 158: 1400-1402; Oct. 1997.

Delk, J. "Early Experience with the American Medical Systems New Tactile Pump: Results of a Multicenter Study" J Sex med 2005; 2: 266-271.

Deuk Choi, Y. et al. "Mechanical Reliability of the AMS 700CXM Inflatable Penile Prosthesis for the Treatment of Male Erectile Dysfunction" J. Urol 168, 822-824, Mar. 2001.

Deveci, S. et al "Penile Length Alterations following Penile Prosthesis Surgery" Europan Urol. 51 (2007) 1128-31.

Gefen, A. "Stresses in the normal and diabetic human penis following implantation of an inflatable prosthesis." Med. Biol., Eng. Comput., 1999, 37, 625-31.

Garber, B. "Inflatable penile prostheses for the treatment of erectile dysfunction." Exper Rev. Med. Devices 2(3), 341-50 (2005).

Gefen, A et al. " A biomechanical model of Peyronie's disease" J. Biomech.33 (2000) 1739-44.

Gefen, A et al. "Optimization of Design and Surgical Positioning of Inflatable Penile Prostheses" Annals of Biomed. Eng. 28 (2000) 619-28.

Henry, G "Advances in Penile Prosthesis Design", Current Sexual Health Reports 2007, 4:15-19.

InhibiZone Antibiotic Surface Treatment, (AMS Brochure) 4pgs. 2001.

Kadioglu, A. et al. "Surgical Treatment of Peyronie's Disease: A Critical Analysis" european urology 50 (2006) 235-248.

"Kava, B et al ""Efficacy and Patient Satisfaction Associated with Penile ProsthesisRevision Surgery""J Sex Med 2007;4:509-518".

Lazarou, S., et al, "Technical Advances in Penile Prostheses" J Long-Term Effects of Med. Imp. 16 (3):235-247 (2006).

Levine, L et al, "Mechanical Reliability and Safety of, and Patient Satisfaction With the Ambicor Inflatable Penile Prosthesis: . . . " J Urol vol. 166, 932-937, Sep. 2001.

Lumen, N. "Phalloplasty: A Valuable Treatment for Males with Penile Insufficiency", Urology 71 (2), 2008 272-276.

Lux, M. et al. "Outcomes and Satisfaction Rates for the Redesigned 2-Piece Penile Prosthesis" J Urol. vol. 177, 262-266, Jan. 2007.

Mentor New from Mentor Urology Alpha I Narrow-Base (Brochure) 2pgs 1996

Mentor Alpha I Inflatable Penile Prosthesis (Brochure) 2 pgs Jul. 1996.

Mentor Surgical Protocol Alpha I Inflatable Penile Prosthesis 17pgs May 1998.

Mentor Patient Guide for Alpha I Inflatable Penile Implant (Brochure) 2pgs 1997.

Montague, D., "Penile Prosthesis Implantation for End-Stage Erectile Dysfunction After Radical Prostatectomy" Reviews in Urol. vol. 7 Suppl. 2 2005 S51-S57.

Mulcahy, J. "Distal Corporoplasty for Lateral Extrusion of Penile Prosthesis Cylinders" J. Urol. vol. 161, 193-195 Jan. 1999.

Murphy, Am., et al. "Failure of the Ambicors inflatable penile prosthesis to deflate" International Journal of Impotence Research (2005) 17, 291-292.

"Parylene Micro Coating" AMS Brochure, 4 pgs 2000.

Sadeghi-Nejad, H. "Penile Prosthesis Surgery: A Review of Prosthetic Devices and Associated Complications" J Sex Med 2007;4:296-309.

Scarzella, IG,. et al. "Use of Amibcor Penile Prosthesis in Peyronie's Disease and as Replacement for Malfunctioning AMS 700 Devices", J Sex Med 2004; Suppl. 1.

Ultrex Plus Penile Prosthesis (AMS Advertisement) 1 pg (1992).

Wang, Shyh-Jen, et al "Hardness evaluation of penile prostheses" International Journal of Urology (2006) 13, 569-572.

Mentor Surgical Protocol Alpha I Inflatable Penile Prosthesis 15pgs 1998.

Mentor Urology Products, (Brochure), Mentor, 20 pages (1998).

Hellstrom, WJG, "Three-piece inflatable penile prosthesis components (surgical pearls on, . . . )" International Journal of Impotence Research (2003) 15, Suppl 5, S136-S138.

Kim, Sae-Chui, "Mechanical Reliability of AMS Hydraulic Penile Prostheses" J. of Korean Med. Sci. 10(6); 422-425, Dec. 1995.

Mooreville, M. et al. Implantation of Inflatable Penile Prosthesis in Patients With Severe Corporeal Fibrosis: Introduction of a New Penile . . . J. Urol 162, 2054-2057, Dec. 1999.

Montague, DK "Cylinder Sizing: less is more" International Journal of Impotence Research (2003) 15, Suppl 5, S132-S133.

Montague, DK et al, "Penile Prosthesis Infections" International Journal of Impotence Research (2001) 13, 326-328.

Malloy, T., et al.,"Improved Mechanical Survival with Revised Model Inflatable Penile Prosthesis Using Rear-Tip Extenders", J Urol. 128 Sep. 1982 489-491.

Chang, Yao-Jen, et al "Penile Prosthesis Implantation" eMedicine http://www.emedicine.com/med/topic3047.htm 19 pages (2003).

Gregory, J., et al., "The Inflatable Penile Prosthesis: Failure of the Rear Tip Extender in Reducing the Incidence of Cylinder Leakage" J Urol. vol. 131 668-669 (1984).

Joseph, D., et al., "Bilateral Disloctin of Rear Tip Extenders from the Inflatable Penile Prosthesis" J Urol vol. 128, Dec. 1982 1317-1318.

Bella, A. et al, "Initial experience with 50 patients using the new AMS 700 with MS Pump Series inflatable penile prosthesis" Poster# 44 J Sex Med, Jan. 2008;5(suppl 1) p. 20.

Durazi,. M, et al. "Penile Prosthesis Implantation for Treatment of Postpriapism Erectile Dysfunctoin" Urol. J. 5 (2) (2008) 115-19.

Eid, J. "What is new for inflatable penile prostheses?" Curr Opin. Urol 19:582-588 (2009).

"Henry, G., et al""Revision Washout Decreases Implant CapsuleTissue Culture Positivity: A Multicenter Study""J Urol. vol. 179, 186-190, Jan. 2008."

Henry, G "Historical Review of Penile Prosthesis Design and Surgical Techniques: Part 1 of a Three-Part Review Series on Penile Prosthetic Surgery" J Sex Med 2009;6:675-681.

Hoebeke, P., et al. "Erectile Implants in Female-to-Male Transsexuals:Our Experience in 129 Patients" Eur Urol (2009), doi:10. 1016/j.eururo.2009.03.013.

Leriche, A., Long-term outcome of forearm flee-lap phalloplasty in the treatment of transsexualism: BJU International 101: 1297-1300 2008.

Nahdrstad, BC "Informed consent for penile prosthesis", International Journal of Impotence Research (2009) 21, 37-50.

Natali, A "Penile Implantation in Europe: Successes and Complications with 253 Implants in Italy and Germany" J Sex Med 2008;5:1503-1512.

Simmons, M. et al "Penile prosthesis implantation: past, present and future", International Journal of Impotence Research (2008) 20, 437-444.

Acu-Form Penile Prosthesis, Mentor, 1 page Aug. 1997.

Agrawal, Wineet et al., An Audit of Implanted Penile Prosthesis in the UK, BJU International pp. 393-395 (2006).

Akand, Murat, Mechanical Failure with Malleable Penile Prosthesis, J. Urol. 70:1007 ell-1007 e12 (2007).

AMS Malleable 600 TM American Medical Systems Publication 30915, 1983.

Anafarta, Kadri, Clinical Experience with Inflatable and Malleable Penile Implants in 104 Patients, Urol. Int. 56:100-104 (1996).

Benson RC Jr., Patterson DE, Barrett DM, Long-term results with the Jonas malleable penile prosthesis. J. Urol. vol. 134, Nov. (1985) pp. 899-901.

Burns-Cox, N., Fifteen Years Experience of Penile Prosthesis Insertion, International J. Impotence Res. (1997) 9, 211-216.

Chiang, Han-Sun, 10 Years Experience with Penile Prosthesis Implantation in Taiwanese Patients, J. Urol. vol. 163:476-480 (2000).

Choi, Hyung Ki, Ten Years of Experience with Various Penile Prosthesis in Korean, Yasei Medical J. vol. 35, No. 2 (1994) 209-217.

Dorflinger T, Bruskewitz R, AMS Malleable Penile Prosthesis, Urology, Dec. 1986; 28(6):480-5.

Fathy, Ahmad, Experience with Tube (Promedon_Malleable Penile Implant, Urol. Int. 2007; 79:244-247.

Ferguson, Kenneth, Prospective Long-Term Results and Quality-of-Life-Assessment After Dura-II Penile Prosthesis Placement, Urol. 61(2) 437-441 (2003).

Fogarty, JD, Cutaneous Temperature Measurements in Men with Penile Prosthesis: A Comparison Study, Int. J. of Impotence Res. (2005) 17,506-509.

Jonas U. Silicone-Silver Penis Prosthesis (Jonas-Eska), Long-Term Reconstruction. J. Urol. Sep. 1998; 160(3 Pt 2):1164-8.

Kardar, A.H., An Unusual Complication of Penile Prosthesis Following Urethroplasty, Scand. J. Urol. Nephrol. 36: 89-90, 2002.

Kaufman, JJ, Raz S. Use of Implantable Prostheses for the Treatment of Urinary Incontinence and Impotence, Am J Surg. Aug. 1975; 130(2):244-50.

Khoudary, Kevin, Design Considerations in Penile Prostheses: The American Medical Systems Product Line, J. Long-Term Effects of Medical Implants, 7(1):55-64 (1997).

Krauss, Dennis J., Use of the Malleable Penile Prosthesis in the Treatment of Erectile Dysfunction: A Prospective Study of Postoperative . . . , J. Urol. vol. 142: 988-991 (1989).

Montague, Drogo, Surgical Approaches for Penile Prostheses Implantation: Penoscrotal VS Infrapubic, International J. Impotence Res. (2003) 15, Suppl. 5, S134-S135.

Morey, Allen et al., Immediate Insertion of a Semirigid Penile Prosthesis for Refractory Ischemic Priapism, Military Medicine, 172, 11:1211, 2007.

Mulcahy, John, Another Look at the Role of Penile Prostheses in the Management of Impotence, Urology Annual 11, pp. 169-185 (1997).

Parulkar, B.G., Revision Surgery for Penile Implants, Int. J. Impotence res. (1994) 6, 17-23.

Pearman, Ro, Insertion of a Silastic Penile Prosthesis for the Treatment of Organic Sexual Impotence. J. Urol. May 1972; 107(5):802-6.

Randrup, Eduardo, Penile Implant Surgery: Rear Tip Extender That Stays Behind, Urology 1992 34, 1 p. 87.

Rhee, Eugene, Technique for Concomitant Implantation of the Penile Prosthesis with the Male Sling. J. Urol. 173:925-927 (2006).

Salama, Nadar, Satisfaction with the Malleable Penile Prosthesis Among Couples from the Middle East: Is it Different . . . , Int. J. Impotence Res. 16:175-180 (2004).

Small, Michael, Small-Carrion Penile Prosthesis: A Report on 160 Cases and Review of the Literature. J. Urol. vol. 167, Jun. 2002 pp. 2357-2360.

Smith, Christopher, Management of Impending Penile Prosthesis Erosion with a Polytetrafluoroethylene Distal Wind Sock Graft, J. Urol. vol. 160: 2037-2040, (1998).

Maul, Judd, Experience with the AMS 600 Malleable Penile Prosthesis, J. Urol. 135:929-931 (1986).

Mentor Urology Products, 18 pages, May 1998.

Merino, G. Atienza, Penile Prosthesis for the Treatment of Erectile Dysfunction, Actas Urol. Esp. 2006: 30(2): 159-169.

Minervini, Andrea, Outcome of Penile Prosthesis Implantation for Treating Erectile Dysfunction: Experience with 504 Procedures, BJU International 97:129-133, (2005).

Montague, Drogo, Clinical Guidelines Panel on Erectile Dysfunction: Summary Report on the Treatment of Organic Erectile Dysfunction, J. Urol. 156:2007-2011 (1996).

Montague, Drogo, Contemporary Aspects of Penile Prosthesis Implantation, Urol. Int. 2003: 70:141-146.

Montague, Drogo, Current Status of Penile Prosthesis Implantation, Urology Reports 2000, 1: 291-296.

Montague, Drogo, Experience with Semirigid Rod and Inflatable Penile Prostheses, J. Urol. 129:967-968, 1983.

Montague, Drogo, Penile Prosthesis Implantation, 712-719, 1994.

Montague, Drogo, Penile Prosthesis Implantation for End-Stage Erectile Dysfunction After Radical Prostatectomy, Reviews in Urol. vol. 7 Suppl. 2 S51-S57, 2005.

Stein, Avi et al., Malleable Penile Prosthesis Removal Leaving Behind the Rear Tip Extenders: A Clinical Presentation, Urol. Int. 50:119-120 (1993).

Surgical Protocol, Mentor 5 pages Sep. 1997.

The AMS Hydroflex Self-Contained Penile Prosthesis, American Medical Systems Publication 50513 (1985).

Yoo JJ, Lee I, Atala A. Cartilage Rods as a Potential Material for Penile Reconstruction, J. Urol. Sep. 1998; 160(3 Pt 2): 1164-8; discussion 1178.

Zerman, Dirk-Henrik, et al., Penile Prosthetic Surgery in Neurologically Impaired Patients: Long-Term Follow-Up, J. Urol. 175; 1041-1044 (2006).

Kimoto, Yasusuke, et al., JSSM Guidelines for Erectile Dysfunction, Int. J. Urol (2008) 15, 564-76.

Natali, Alessandro, et al., Penile Implantation in Europe: Successes and Complications with 253 Implants in Italy and Germany, J Sex. Med. 2008;5: 1503-12.

Montague, DK et al., "Future considerations: advances in the surgical management of erectile dysfunction", International J. Impotence Res. (2000) 12, Suppl 4, S140-S143.

CORRUGATED EXPANSION-CONSTRAINING SLEEVE FOR AN INFLATABLE PENILE PROSTHESIS CYLINDER

CLAIM TO PRIORITY

The present application claims priority to U.S. Provisional Patent Application No. 60/987,136, filed Nov. 12, 2007, and entitled "Corrugated Expansion-Constraining Sleeve for an Inflatable Penile Prosthesis Cylinder." The afore-mentioned provisional patent application is hereby incorporated by reference in its entirety.

FIELD OF THE INVENTION

The present invention relates to implantable penile prosthesis' and, more particularly, to accommodating the expansion caused by inflation of the prosthesis.

BACKGROUND OF THE INVENTION

One common treatment for male erectile dysfunction includes the implantation of a penile implant device. One type of penile implant device includes a pair of cylindrical prostheses that are implanted into the corpus cavernosae of the penis. Typically, the cylindrical prostheses or cylinders are inflatable and are connected to a fluid-filled reservoir through a pump and valve assembly. With one such type of system, one tube extends from each of the two cylindrical prostheses and connects to the pump, and one tube connects the pump to the reservoir. The pump is typically surgically implanted into the scrotum of the patient and the reservoir is implanted in the abdomen, with the tubes fluidly connecting the components. To activate the penile implant device, the patient actuates the pump using one of a variety of methods that cause fluid to be transferred from the reservoir through the pump and into the cylindrical prostheses. This results in the inflation of the prostheses and produces rigidity for a normal erection. Then, when the patient desires to deflate the prostheses, a valve assembly within the pump is actuated in a manner such that the fluid in the prostheses is released back into the reservoir. This deflation returns the penis to a flaccid state.

It is desirable that both the radial and longitudinal expansion of the cylindrical prosthesis be accommodated to constrain and prevent over-expansion.

SUMMARY OF THE INVENTION

An inflatable penile prosthesis cylinder of the present invention includes an inflatable chamber and a constraining sleeve of fabric. The inflatable chamber is configured to expand in response to an increase in pressure within the chamber. The sleeve of fabric constrains the expansion of the chamber, however, the sleeve of fabric includes a corrugation that facilitates some expansion of the sleeve.

The sleeve of fabric may be made of non-distensible yarn and/or distensible yarn. And, preferably includes corrugations that encircle the sleeve. The corrugations are preferably within a plane that is transverse to a longitudinal axis of the sleeve and that is more preferably perpendicular to the longitudinal axis. The corrugations preferably extend along the sleeve in a longitudinal direction that is substantially parallel to a longitudinal axis of the sleeve. In one embodiment, the corrugations are radial corrugations that encircle the sleeve and are longitudinal corrugations that extend in a longitudinal direction that is substantially parallel to a longitudinal axis of the sleeve.

The present invention further includes a method of constraining the expansion of a an inflatable penile prosthesis cylinder from a deflated state to an inflated state. The cylinder includes a cylindrically shaped pressure chamber that is configured to expand and a sleeve of fabric that is configured to constrain the expansion of the pressure chamber. The sleeve includes a number of corrugations. The method includes the steps of: (1) providing the penile prosthesis cylinder in a deflated state in which first portions of an interior surface of the sleeve engage an exterior surface of the pressure chamber and second portions of the interior surface of the sleeve are displaced from the exterior surface of the pressure chamber, due to corrugations, by a distance D; (2) expanding the pressure chamber in response to an increase in pressure within the chamber to a second inflated state; (3) collapsing the corrugations in response to the expanding step, thereby reducing the distance D to a distance D'; and (4) restraining further expansion of the pressure chamber.

The corrugations are preferably longitudinal corrugations that extend substantially parallel to the longitudinal axis of the pressure chamber and are additionally radial corrugations circling the sleeve.

DESCRIPTION OF THE PREFERRED EMBODIMENTS

Various types of penile prosthesis are currently available to cure or compensate for impotence, two of which include a non-inflatable, semi-rigid implantable prosthesis and an inflatable, implantable prosthesis. The non-inflatable, semi-rigid prosthesis is implanted within the corpora cavernosa of the penis and provides a generally constant erection. The inflatable prosthesis is also implanted in the corpora cavernosa but is connected to a hydraulic pumping device. The hydraulic pumping device is located within the patient's body and is used to inflate the prosthesis for erection and deflate the prosthesis for flaccidity. Two exemplary inflatable penile prostheses include the AMS Ambicor® and AMS 700™ Series.

Figure 1:
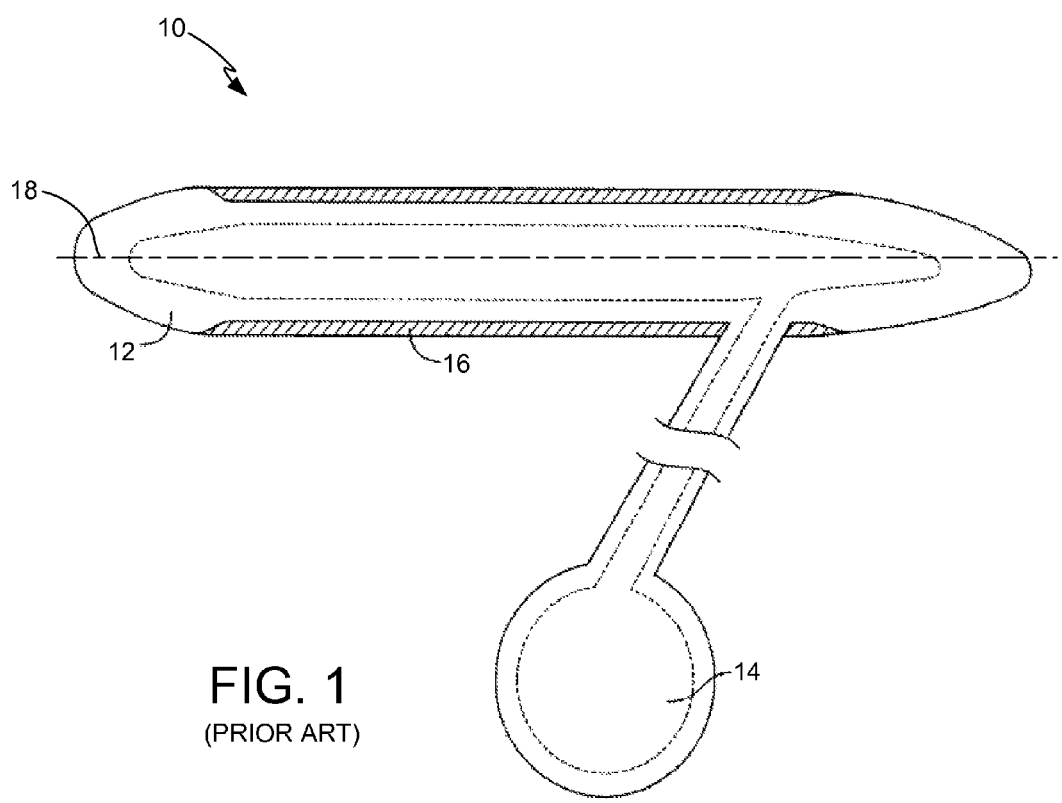
FIG. 1 depicts an inflatable penile prosthesis.
Figure 2:
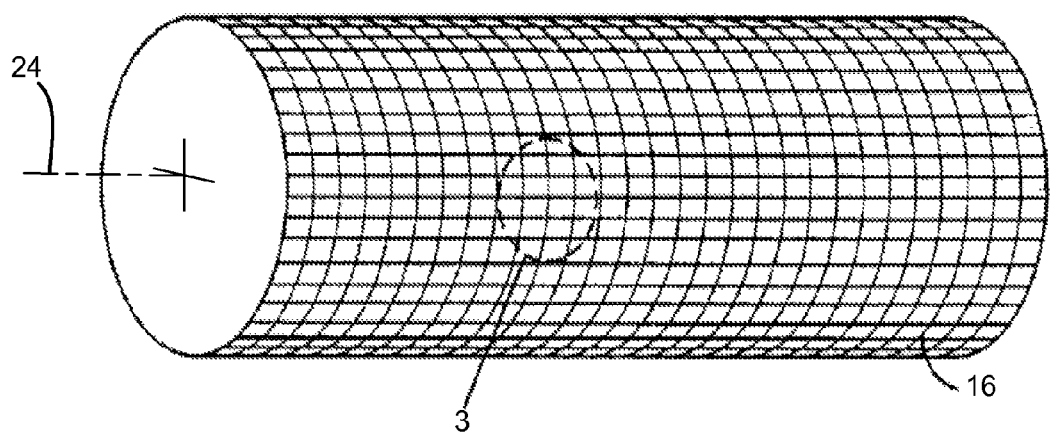
FIG. 2 depicts a sleeve of fabric.

Inflatable, implantable prostheses commonly include two inflatable cylinders: one for each channel of the corpora cavernosa. Each cylinder 10 includes a cylindrically shaped pressure chamber 12 made of silicone and a pump 14 that is used to inflate or deflate the chamber, as illustrated in FIG. 1. The chamber 12 is encapsulated in a sleeve or sheath of biocompatible material (e.g. fabric) that constrains the expansion of the silicone pressure chamber 12. FIG. 2 is a perspective view of an exemplary sleeve of fabric 16 for constraining expansion of the chamber 12. The chamber 12 and the sleeve 16 are typically encapsulated by an expandable silicone shell (not shown) or tube that prevents tissue interaction with the sleeve 16.

Current designs of pressure chambers 12 are configured to expand in a radial direction (i.e., increase in diameter or girth) that is perpendicular to a longitudinal axis 18 of the cylinder or expand both in the radial direction and in a longitudinal direction (i.e., increase in length) that is parallel to the longitudinal axis 18. The sleeves of fabric 16 that encapsulate these types of cylinders must accommodate one or both types of expansion.

Figure 3:
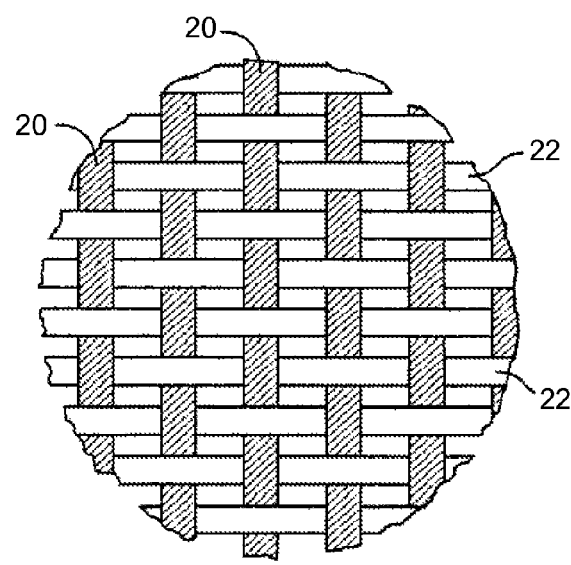
FIG. 3 is a magnified view of the sleeve of FIG. 2

FIG. 3 is a magnified view of the sleeve 16 within circle 3 of FIG. 2. The fabric includes yarn 20 circling the sleeve 16 (i.e., running circumferentially) and yarn 22 running in the lengthwise or longitudinal direction defined by the longitudinal axis 24 of the sleeve 16, which is aligned with longitudinal axis 18 of the chamber 12 (FIG. 1). The yarn 20 and 22 can be distensible (fill) or non-distensible (warp) type of yarn. The "non-distensible" yarn describes a type of yarn that is substantially non-distensible at the operating pressures of the cylinder 12. That is, the inflation of the cylinder 12 will not impose pressures within the non-distensible yarn that will cause it to stretch a significant amount. Exemplary non-distensible yarns comprise polyester or other materials having a high modulus of elasticity.

The distensible yarn generally comprises a distensible thread (e.g., an elastomer thread) around which a non-distensible thread is coiled. The distensible yarn is capable of stretching in response to the expansion of the chamber 12 to a limit imposed by the non-distensible thread.

The conventional manner in which the sleeve 16 accommodates radial expansion of the chamber 12 is to utilize distensible yarn for yarn 20 and non-distensible yarn for the yarn 22. As the chamber 12 expands in the radial direction, the distensible yarn 20 stretches to accommodate expansion in the radial direction while the yarn 22 constrains expansion of the chamber 12 in the longitudinal direction. When the chamber 12 is deflated, the distensible yarn 20 contracts.

The conventional manner in which sleeve 16 accommodates both radial and longitudinal expansion of the chamber 12 is to utilize distensible yarn for the yarn 20 and the yarn 22. Accordingly, the yarn 20 stretches to accommodate radial expansion of the chamber 12 and the yarn 22 stretches to accommodate longitudinal expansion of the chamber 12. When the chamber 12 is deflated, the distensible yarn 20 and 22 contract.

FIGS. 4A-4D, 5 and 6 illustrate sleeves of fabric 30 for use in constraining an inflatable pressure chamber, such as the exemplary cylinder 12 shown in FIG. 1, of a penile prosthesis cylinder 10 in accordance with embodiments of the invention. It should be noted that the outer tube that typically surrounds the sleeve 30 is not shown in order to simplify the illustrations.

In general, the sleeve 30 includes one or more corrugations 32 that accommodate radial and/or longitudinal expansion of the chamber 12. The corrugations 32 can be formed by any suitable method. Exemplary methods include heating the fabric while it is shaped with the corrugations and later forming the sleeve 30 with the corrugated fabric, heating the assembled sleeve 30 within a mold that defines the desired corrugations 32, or other suitable method.

Embodiments of the fabric used to form the sleeve 30 can include distensible yarns to accommodate both radial and/or longitudinal expansion, as described above. In accordance with one embodiment, the fabric used to form the sleeve 30 is formed of non-distensible yarns such that the threads of the fabric are not distensible under normal pressures applied to the sleeve 30 during the expansion of the chamber 12.

Figure 4A:
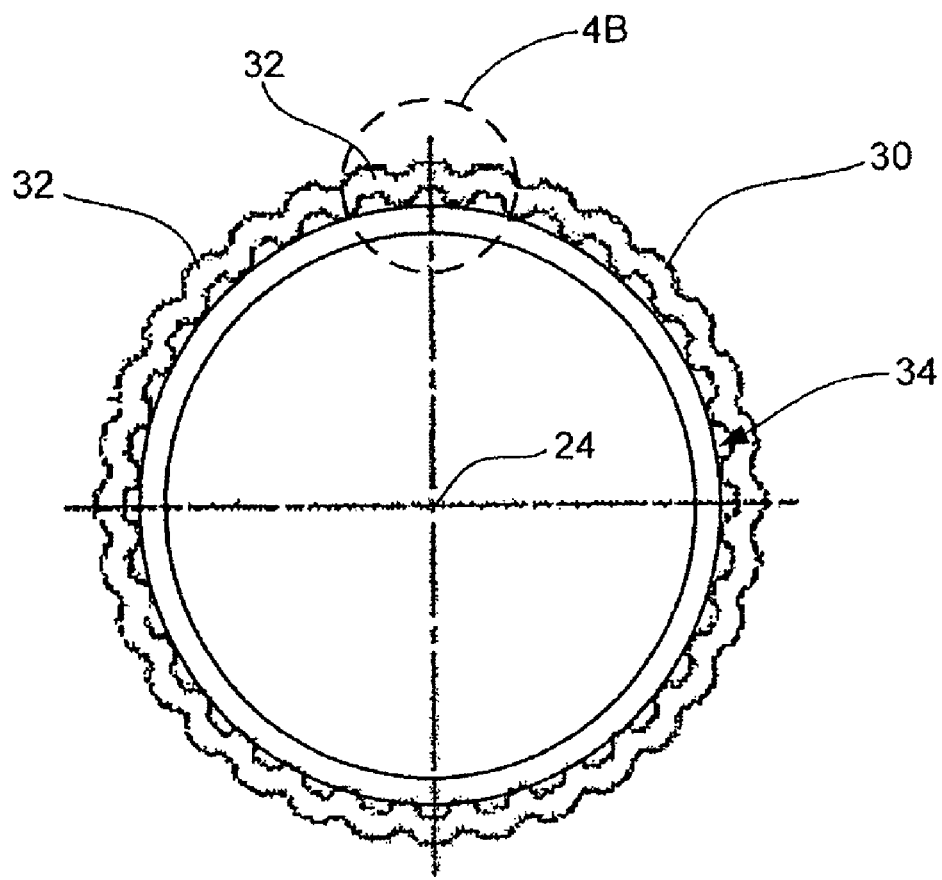
FIG. 4A depicts a sleeve having longitudinal corrugations (deflated).
Figure 4B:
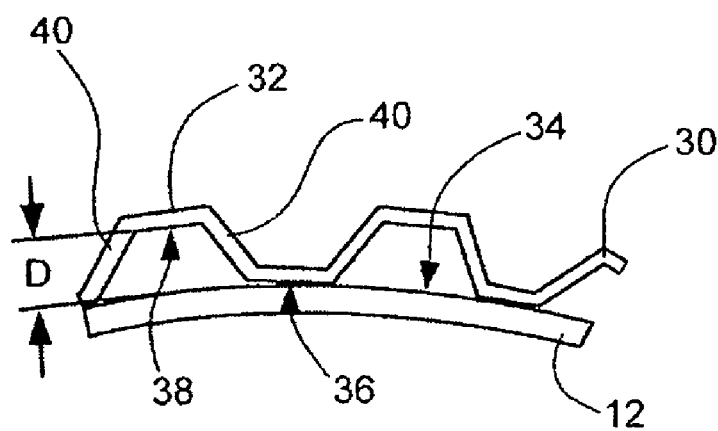
FIG. 4B is a magnified view of the sleeve of FIG. 4A (deflated).

FIG. 4A is a front cross-sectional view of one embodiment of the sleeve 30 that includes longitudinal corrugations 32 that run in the longitudinal direction (i.e., approximately parallel to longitudinal axis 24) of the sleeve 30. The sleeve 30 shown in FIG. 4A is in a deflated state. The deflated state of the sleeve 30 corresponds to a deflated state of the pressure chamber 12. When in the deflated state, the exterior surface 34 of the pressure chamber 12 engages portions 36 of the interior surface of the sleeve 30, as best shown in FIG. 4B, which is a magnified view of the sleeve 30 and chamber 12 approximately within circle 4B of FIG. 4A.

Additionally, portions 38 of the interior surface of the sleeve 30 are displaced from the exterior surface 34 of the chamber 12 a distance D, when the sleeve 30 and the chamber 12 are in their deflated states. The distance D is determined by the depth of the sides 40 of the corrugations 32 and the amount that the sides 40 are stretched apart when the chamber 12 is in its deflated state.

Figure 4C:
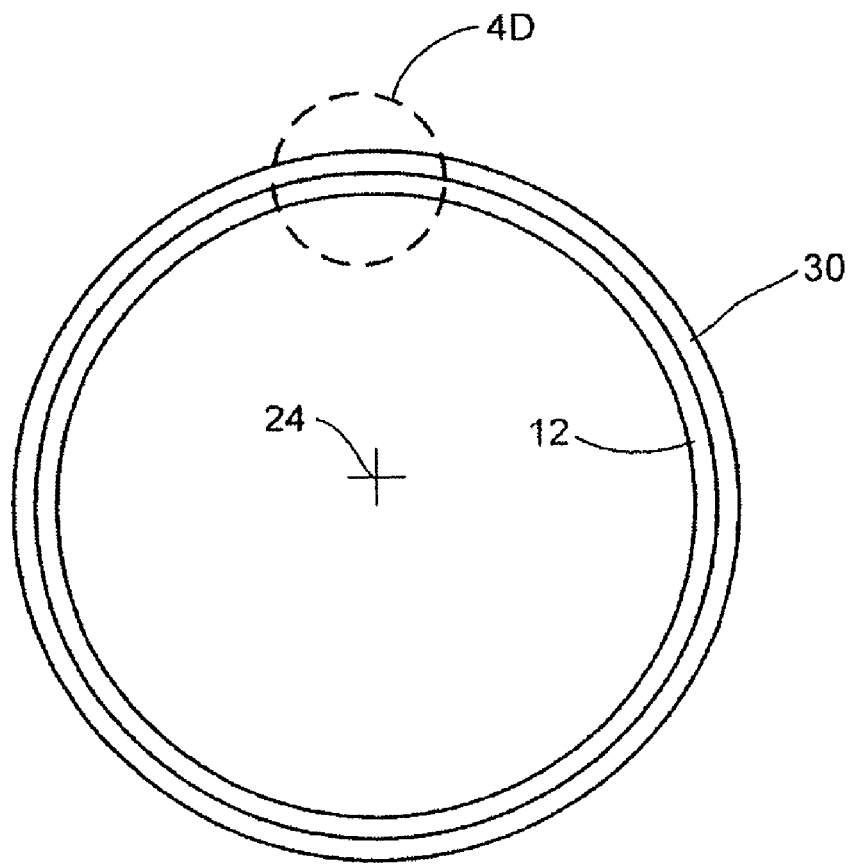
FIG. 4C depicts the sleeve of FIG. 4A in an inflated state.
Figure 4D:
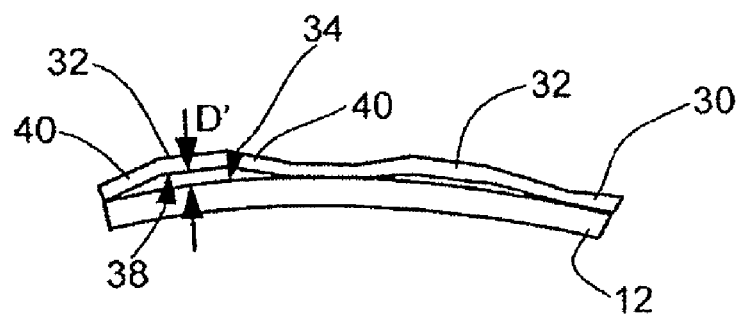
FIG. 4D is a magnified view of the sleeve of FIG. 4A.

As the chamber 12 expands radially in response to an increase in pressure within the chamber 12, the chamber 12 and the sleeve 30 reach an inflated state that is illustrated in the cross-sectional view of FIG. 4C. During the expansion of the chamber 12, the corrugations 32 collapse resulting in a reduction of the distance D to the distance D', illustrated in FIG. 4D, which is a magnified view of the portion within circle 4D of FIG. 4C. The distance D' is dependent upon the pressure applied to the sleeve 30 by the chamber 12, the material used to form the sleeve 30, and other factors.

The amount of expansion the sleeve 30 undergoes as a result of the collapse of the corrugations 32 depends on the number of corrugations 32 and the change in the distance D (i.e., D-D'). The more corrugations 32 in the sleeve 30, the greater the expansion that the sleeve 30 can undergo. The greater the change in the distance D, the greater the expansion that the sleeve 30 can undergo.

The expansion of the chamber 12 is constrained by the spring-like force generated by the corrugations 32 that motivates their return to a quiescent state, which is proximate the deflated state, and the material used to form the sleeve 30, which may or may not include distensible yarn as mentioned above. Additionally, the outer tube (not shown) that surrounds the sleeve 30 in the fully constructed cylinder can also help to motivate the return of the corrugations to their quiescent state.

Figure 5:
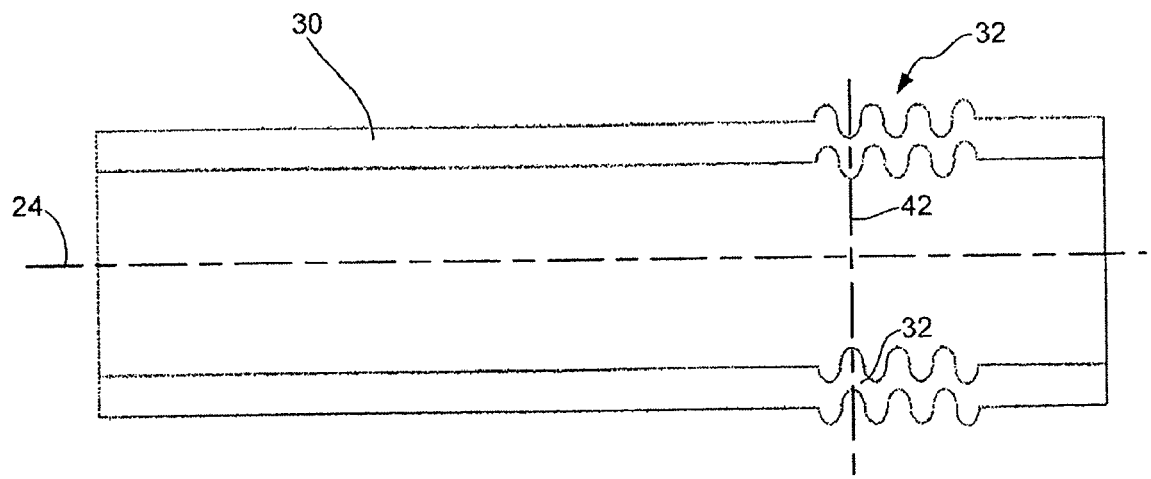
FIG. 5 depicts a sleeve having radial corrugations.
Figure 6:
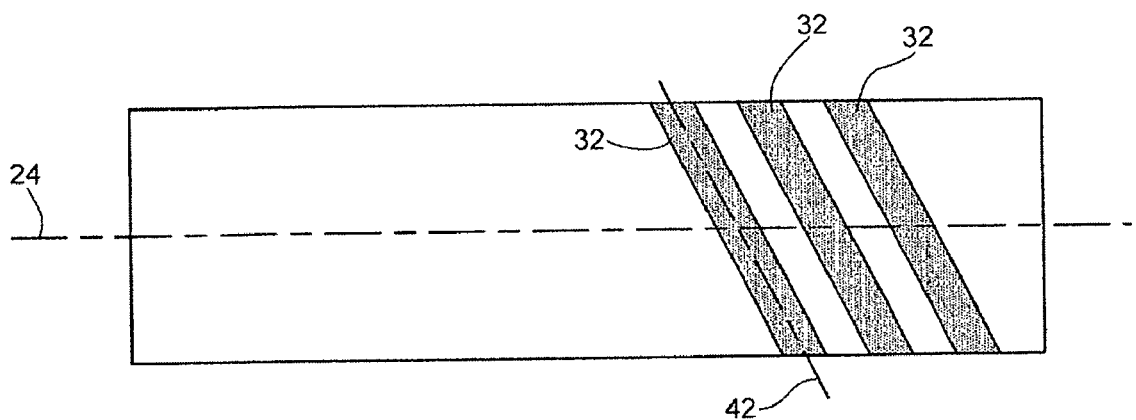
FIG. 6 depicts a sleeve having corrugations oriented transversely to the longitudinal axis.

In accordance with another embodiment of the invention, the corrugations 32 in the sleeve 30 include radial corrugations 32 that circle the longitudinal axis 24, as shown in the side cross-sectional view of FIG. 5. The radial corrugations 32 allow the sleeve 30 to expand in the longitudinal direction through the collapsing of the corrugations 32, as explained above. Thus, the sleeve 30 can accommodate a longitudinal expansion of the chamber 12 without the need for distensible yarn running in the longitudinal or lengthwise direction (FIG. 3).

In one embodiment, each corrugation 32 encircles the sleeve 30. In another embodiment, the corrugations 32 are each within a plane 42 that is oriented perpendicularly to the longitudinal axis 24, as shown in FIG. 5. In another embodiment, the corrugations are within a plane 44 that is oriented transversely to the longitudinal axis 24, but not perpendicularly to the longitudinal axis 24, as illustrated in the side view of FIG. 6.

In one embodiment, the sleeve 30 includes the material illustrated in FIG. 3 having distensible yarn 20 running in the circumferential direction, which accommodates radial expansion of the chamber 12 while the corrugations 32 accommodate the longitudinal expansion of the chamber 12.

In yet another embodiment, the sleeve 30 includes both longitudinal and radial corrugations to accommodate both radial and longitudinal expansion of the chamber 12. The material used to form this embodiment of the sleeve 30 can also include distensible yarns to further accommodate radial and or longitudinal expansion of the chamber.

Although the present invention has been described with reference to preferred embodiments, workers skilled in the art will recognize that changes may be made in form and detail without departing from the spirit and scope of the invention. For example, it is understood by those skilled in the art that embodiments of the invention include each of the embodiments of the sleeve of fabric 30 described above alone and in combination with other embodiments of the sleeve 30 and without being combined with the pressure chamber 12 or other components of penile prostheses.

What is claimed is:

1. An inflatable penile prosthesis cylinder comprising:
  an inflatable chamber having a longitudinal axis and configured to expand in response to an increase in pressure within the chamber; and
  a sleeve of fabric that constrains the expansion of the chamber, the sleeve of fabric comprising non-distensible yarn having a plurality of corrugations that extend across the yarn and accommodate expansion of the sleeve of fabric.

2. The cylinder of claim 1, wherein the sleeve of fabric further comprises a distensible yarn interwoven with the non-distensible yarn.

3. The cylinder of claim 1, wherein the corrugations accommodate radial expansion of the sleeve relative to the longitudinal axis.

4. The cylinder of claim 3, wherein the non-distensible yarn extends in a plane that is transverse to the longitudinal axis.

5. The cylinder of claim 1, wherein the corrugations accommodate longitudinal expansion of the sleeve along the longitudinal axis.

6. The cylinder of claim 1, wherein the non-distensible yarn extends in a plane that substantially parallel to the longitudinal axis.

7. The cylinder of claim 1, wherein:
  the non-distensible yarn extends in a plane that is transverse to the longitudinal axis and in a plane that is substantially parallel to the longitudinal axis; and
  the corrugations accommodate both radial expansion of the sleeve and longitudinal expansion of the sleeve relative to the longitudinal axis.

8. An inflatable penile prosthesis cylinder comprising:
  an inflatable chamber having a longitudinal axis and configured to expand in response to an increase in pressure within the chamber; and
  a sleeve of fabric comprising a non-distensible yarn having a plurality of corrugations that accommodate radial expansion of the chamber relative to the longitudinal axis.

9. The cylinder of claim 8, wherein the sleeve of fabric further comprises a distensible yarn that is interwoven with the non-distensible yarn.

10. The cylinder of claim 8, wherein the corrugations accommodate longitudinal expansion of the sleeve along the longitudinal axis.

11. The cylinder of claim 8, wherein the corrugations extend along the sleeve in a longitudinal direction that is substantially parallel to the longitudinal axis.

12. The cylinder of claim 8, wherein the corrugations include radial corrugations that encircle the sleeve and longitudinal corrugations that extend along the sleeve in a longitudinal direction that is substantially parallel to the longitudinal axis.

13. An inflatable penile prosthesis cylinder comprising:
  a cylindrically shaped pressure chamber configured to expand in a radial direction that is perpendicular to a longitudinal axis of the pressure chamber and a longitudinal direction that is parallel to the longitudinal axis; and
  a sleeve of fabric comprising a non-distensible yarn that constrains the expansion of the pressure chamber, the sleeve including a plurality of radial corrugations formed in the non-distensible yarn encircling the sleeve and a plurality of longitudinal corrugations formed in the non-distensible yarn extending in the longitudinal direction.

14. The cylinder of claim 13, wherein the sleeve of fabric further comprises distensible yarn interwoven with the distensible yarn.

15. The cylinder of claim 13, wherein the radial corrugations are each within a plane that is transverse to the longitudinal axis.

16. The cylinder of claim 15, wherein each of the planes is perpendicular to the longitudinal axis.

17. A method of constraining expansion of an inflatable penile prosthesis cylinder from a deflated state to an inflated state, the cylinder including a cylindrically shaped pressure chamber having a longitudinal axis configured to expand and a sleeve of fabric configured to constrain the expansion of the pressure chamber, the sleeve comprising non-distensible yarn having a plurality of corrugations, the method comprising steps of:
  providing the penile prosthesis cylinder in a deflated state in which first portions of an interior surface of the sleeve engage an exterior surface of the pressure chamber and second portions of the interior surface of the sleeve are displaced from the exterior surface of the pressure chamber, due to the corrugations, by a distance D;
  expanding the pressure chamber in the radial direction relative to the longitudinal axis in response to an increase in pressure within the chamber to a second inflated state;
  collapsing the corrugations in response to the expanding step, thereby reducing the distance D to a distance D'; and
  restraining further expansion of the pressure chamber using the sleeve.

18. The method of claim 17, wherein:
  the pressure chamber is further configured to expand in a longitudinal direction;
  the corrugations comprise radial corrugations circling the sleeve; and
  the expanding step includes expanding the pressure chamber in the longitudinal direction.

* * * * *